(12) United States Patent
Locke et al.

(10) Patent No.: US 10,286,122 B2
(45) Date of Patent: May 14, 2019

(54) SYSTEMS AND METHODS FOR TUBE MANAGEMENT

(71) Applicant: LifeCell Corporation, Branchburg, NJ (US)

(72) Inventors: Christopher Locke, Bournemouth (GB); James Seddon, Ferndown (GB); Benjamin A. Pratt, Poole (GB); Evan Friedman, Montvale, NJ (US); Aaron Barere, Hoboken, NJ (US)

(73) Assignee: LifeCell Corporation, Madison, NJ (US)

( * ) Notice: Subject to any disclaimer, the term of this patent is extended or adjusted under 35 U.S.C. 154(b) by 308 days.

(21) Appl. No.: 15/299,966

(22) Filed: Oct. 21, 2016

(65) Prior Publication Data

US 2017/0112976 A1    Apr. 27, 2017

Related U.S. Application Data

(60) Provisional application No. 62/244,398, filed on Oct. 21, 2015.

(51) Int. Cl.
| | |
|---|---|
| *A61M 39/28* | (2006.01) |
| *A61M 1/00* | (2006.01) |
| *C12M 1/33* | (2006.01) |
| *A61B 17/00* | (2006.01) |
| *A61B 18/00* | (2006.01) |

(52) U.S. Cl.
CPC ........ *A61M 1/0035* (2014.02); *A61M 1/0001* (2013.01); *A61M 1/0058* (2013.01); *A61M 1/0094* (2014.02); *A61M 39/28* (2013.01); *A61B 2017/00792* (2013.01); *A61B 2018/00464* (2013.01); *A61M 2202/08* (2013.01); *C12M 45/02* (2013.01)

(58) Field of Classification Search
CPC .. A61M 39/28; A61M 39/286; A61M 39/287; A61M 1/0035; A61M 1/0094; A61M 1/0001; A61B 2018/00464
See application file for complete search history.

(56) References Cited

U.S. PATENT DOCUMENTS 3,791,524 A    2/1974 Cho
3,855,997 A  * 12/1974 Sauer ................. A61B 10/0045
                                                                215/309

(Continued)

FOREIGN PATENT DOCUMENTS

EP           0512769 A2     11/1992
JP        2009189282 A  *   8/2009  ............ C12M 33/10

(Continued)

OTHER PUBLICATIONS

Translation of JP 2009189282.*

(Continued)

*Primary Examiner* — Adam Marcetich
*Assistant Examiner* — Jessica R Arble
(74) *Attorney, Agent, or Firm* — McCarter & English, LLP; Matthew R. Van Eman

(57) ABSTRACT

Systems, devices, and methods of the present disclosure assist with management of tubes and hoses during surgical procedures. The systems, devices, and methods provide for the proper opening and closing of tubes to facilitate performance of steps in a surgical procedure.

23 Claims, 8 Drawing Sheets

(56) References Cited

U.S. PATENT DOCUMENTS

| | | | |
|---|---|---|---|
| 4,457,339 A * | 7/1984 | Juan | F16K 7/065 137/624.16 |
| 4,681,571 A | 7/1987 | Nehring | |
| 4,753,634 A | 6/1988 | Johnson | |
| 4,821,996 A * | 4/1989 | Bellotti | A61M 39/223 251/230 |
| 4,988,623 A | 1/1991 | Schwarz et al. | |
| 5,301,685 A | 4/1994 | Guirguis | |
| 5,330,914 A | 7/1994 | Uhlen et al. | |
| 5,336,616 A | 8/1994 | Livesey et al. | |
| 5,372,945 A | 12/1994 | Alchas et al. | |
| 5,409,833 A | 4/1995 | Hu et al. | |
| 5,601,707 A | 2/1997 | Clay et al. | |
| 5,610,074 A | 3/1997 | Beritashvili et al. | |
| 5,785,640 A | 7/1998 | Kresch et al. | |
| 5,786,207 A | 7/1998 | Katz et al. | |
| D401,336 S | 11/1998 | Muller et al. | |
| 5,853,398 A * | 12/1998 | Lal | A61M 5/1412 604/250 |
| 5,901,717 A | 5/1999 | Dunn et al. | |
| 5,968,356 A | 10/1999 | Morsiani et al. | |
| D424,194 S | 5/2000 | Holdaway et al. | |
| 6,200,606 B1 | 3/2001 | Peterson et al. | |
| 6,258,054 B1 | 7/2001 | Mozsary et al. | |
| 6,261,549 B1 | 7/2001 | Fernandez et al. | |
| 6,478,966 B2 | 11/2002 | Zhou et al. | |
| 6,544,788 B2 | 4/2003 | Singh | |
| 6,733,537 B1 | 5/2004 | Fields et al. | |
| D492,995 S | 7/2004 | Rue et al. | |
| 6,852,533 B1 | 2/2005 | Rafii et al. | |
| 7,172,572 B2 | 2/2007 | Diamond et al. | |
| 7,361,368 B2 | 4/2008 | Claude et al. | |
| 7,390,484 B2 | 6/2008 | Fraser et al. | |
| D575,393 S | 8/2008 | Stephens | |
| 7,429,488 B2 | 9/2008 | Fraser et al. | |
| 7,473,420 B2 | 1/2009 | Fraser et al. | |
| 7,501,115 B2 | 3/2009 | Fraser et al. | |
| 7,514,075 B2 | 4/2009 | Hedrick et al. | |
| 7,585,670 B2 | 9/2009 | Hedrick et al. | |
| 7,588,732 B2 | 9/2009 | Buss | |
| 7,595,043 B2 | 9/2009 | Hedrick et al. | |
| 7,651,684 B2 | 1/2010 | Hedrick et al. | |
| 7,687,059 B2 | 3/2010 | Fraser et al. | |
| 7,708,152 B2 | 5/2010 | Dorian et al. | |
| 7,732,190 B2 | 6/2010 | Michal et al. | |
| 7,744,820 B2 | 6/2010 | Togawa et al. | |
| 7,749,741 B2 | 7/2010 | Bullen et al. | |
| 7,780,649 B2 | 8/2010 | Shippert | |
| 7,780,860 B2 | 8/2010 | Higgins et al. | |
| 7,789,872 B2 | 9/2010 | Shippert | |
| 7,794,449 B2 | 9/2010 | Shippert | |
| 7,887,795 B2 | 2/2011 | Fraser et al. | |
| 7,901,672 B2 | 3/2011 | Fraser et al. | |
| 8,062,286 B2 | 11/2011 | Shippert | |
| 8,100,874 B1 | 1/2012 | Jordan et al. | |
| 8,292,839 B2 * | 10/2012 | O'Neill | A61M 1/3664 422/44 |
| 8,293,532 B2 | 10/2012 | Moynahan | |
| 8,333,740 B2 | 12/2012 | Shippert | |
| 8,337,711 B2 | 12/2012 | Dorian et al. | |
| 8,366,694 B1 | 2/2013 | Jordan | |
| D679,011 S | 3/2013 | Kitayama et al. | |
| 8,409,860 B2 | 4/2013 | Moynahan | |
| D683,851 S | 6/2013 | Greenhalgh | |
| D687,549 S | 8/2013 | Johnson et al. | |
| D692,559 S | 10/2013 | Scheibel et al. | |
| 8,622,997 B2 | 1/2014 | Shippert | |
| 8,632,498 B2 | 1/2014 | Rimsa et al. | |
| 8,887,770 B1 | 11/2014 | Shippert | |
| 2001/0030152 A1 | 10/2001 | Wright et al. | |
| 2002/0188280 A1 | 12/2002 | Nguyen et al. | |
| 2004/0005246 A1 | 1/2004 | Efthimiadis et al. | |
| 2004/0097867 A1 | 5/2004 | Fraser et al. | |
| 2005/0084961 A1 | 4/2005 | Hedrick et al. | |
| 2005/0131335 A1 * | 6/2005 | Drott | A61M 39/223 604/9 |
| 2006/0051865 A1 | 3/2006 | Higgins et al. | |
| 2006/0184119 A1 | 8/2006 | Remde et al. | |
| 2006/0224144 A1 | 10/2006 | Lee | |
| 2007/0106208 A1 | 5/2007 | Uber et al. | |
| 2007/0225665 A1 | 9/2007 | Perez-Cruet et al. | |
| 2007/0248575 A1 | 10/2007 | Connor et al. | |
| 2008/0014181 A1 | 1/2008 | Ariff et al. | |
| 2008/0050275 A1 | 2/2008 | Bischof et al. | |
| 2009/0042267 A1 | 2/2009 | Park | |
| 2009/0181104 A1 | 7/2009 | Rigotti et al. | |
| 2009/0287190 A1 | 11/2009 | Shippert | |
| 2009/0299328 A1 | 12/2009 | Mudd et al. | |
| 2010/0174162 A1 | 7/2010 | Gough et al. | |
| 2010/0268189 A1 | 10/2010 | Byrnes et al. | |
| 2010/0285521 A1 | 11/2010 | Vossman et al. | |
| 2010/0285588 A1 | 11/2010 | Stubbers et al. | |
| 2011/0009822 A1 | 1/2011 | Nielsen | |
| 2011/0117650 A1 | 5/2011 | Riordan | |
| 2011/0198353 A1 | 8/2011 | Tsao | |
| 2012/0003733 A1 | 1/2012 | Gueneron | |
| 2012/0214659 A1 | 8/2012 | Do et al. | |
| 2013/0131635 A1 | 5/2013 | Rimsa et al. | |
| 2013/0150825 A1 | 6/2013 | Rimsa et al. | |
| 2013/0158515 A1 | 6/2013 | Austen, Jr. | |
| 2013/0324966 A1 | 12/2013 | Park et al. | |
| 2014/0363891 A1 | 12/2014 | Llull et al. | |
| 2018/0057787 A1 | 3/2018 | Friedman et al. | |

FOREIGN PATENT DOCUMENTS

| | | |
|---|---|---|
| JP | 201112581 A | 1/2011 |
| WO | 2008/137234 A1 | 11/2008 |
| WO | 2009/055610 A1 | 4/2009 |
| WO | 2009/149250 A1 | 12/2009 |
| WO | 2011052946 A2 | 5/2011 |
| WO | 2012006587 A2 | 1/2012 |
| WO | 2012/019103 A2 | 2/2012 |
| WO | 2012/083412 A1 | 6/2012 |
| WO | 2012/109603 A1 | 8/2012 |
| WO | 2012/116100 A1 | 8/2012 |
| WO | 2012/139593 A2 | 10/2012 |
| WO | 2013090579 A1 | 6/2013 |
| WO | 2013106655 A1 | 7/2013 |

OTHER PUBLICATIONS

Coleman et al.; "Fat Grafting to the Breast Revisited: Safety and Efficacy;" Plastic and Reconstructive Surgery; 119(3):775-785 (Mar. 2007).

Delay et al.; "Fat Injection to the Breast: Technique, Results and Indications Based on 880 Procedures Over 10 Years;" Aesthetic Surgery Journal; 29(5):360-376 (Sep./Oct. 2009).

International Preliminary Report on Patentability; dated Dec. 11, 2014 in the International Patent Application No. PCT/US2013/041111.

Pakhomov et al.; "Hydraulically Coupled Microejection Technique for Precise Local Solution Delivery in Tissues;" J. Neurosci Methods; 155(2):231-240 [Abstract] (Sep. 15, 2006).

Smith et al.; "Autologous Human Fat Grafting: Effect of Harvesting and Preparation Techniques on Adipocyte Graft Survival;" Plastic and Reconstructive Surgery; 117(6):1836-1844 (2006).

Ting et al.; "A New Technique to Assist Epidural Needle Placement" Anesthesiology; 112(5):1128-1135 (May 2010).

Yoshimura et al.; "Cell-Assisted Lipotransfer for Cosmetic Breast Augmentation: Supportive Use of Adipose-derived Stem/Stromal Cells;" Aesthetic Plastic Surgery Journal; 32:48-55 (2008).

International Search Report and Written Opinion for Application No. PCT/US2016/058171, dated Apr. 25, 2017. 14 pages.

International Search Report and Written Opinion for Application No. PCT/US2017/048898, dated Dec. 6, 2017. 13 pages.

International Search Report for Application No. PCT/US2016/058158, dated Feb. 3, 2017. 3 pages.

(56) References Cited

OTHER PUBLICATIONS

International Preliminary Report on Patentability for Application No. PCT/US2016/058158, dated May 3, 2018. 8 pages.

* cited by examiner

| INPUTS | LIPOSUCTION | HOLD AND MIX | IRRIGATION | VACUUM / CLEAR |
|---|---|---|---|---|
| LIPOSUCTION CANNULA | OPEN | CLOSED | CLOSED | CLOSED |
| IRRIGATION TUBE | CLOSED | CLOSED | OPEN | CLOSED |
| VACUUM TUBE | OPEN | CLOSED | CLOSED | OPEN |
| VENT | CLOSED | CLOSED | OPEN | OPEN |

*FIG. 4*

SYSTEMS AND METHODS FOR TUBE MANAGEMENT

This application claims priority to U.S. Provisional Patent Application 62/244,398, which was filed on Oct. 21, 2015, and which is incorporated by reference in its entirety.

Some surgical procedures require use of tubes, hoses, or other conduits to transfer fluids, gases, and/or tissue products between a patient and a treatment system or device, or among systems and devices. Some surgical procedures are multi-step processes requiring connection and disconnection of hoses from input and output ports. For example, using some adipose tissue transfer systems, surgical personnel may need to perform over one hundred combined user actions and decisions. Some of these user actions involve enabling and disabling a vacuum source or adding or removing tissue or washing solutions to a tissue storage and treatment container.

Keeping track of the state of tube connections in some surgical procedures creates a burden on the practitioner. The user effort needed to manage the tube connections is not negligible and can increase the total time to perform procedures. Although organizational technologies such as color-coding exist, they cannot eliminate the burden of needing to assess the state of each individual tube at multiple points throughout a procedure.

In an embodiment of the present invention, a tissue treatment system includes a container and a tube management device. The container includes an exterior wall surrounding an interior volume for holding tissue and a filter for processing tissue. The tube management device includes a tube restrictor plate having a plurality of tube through-holes and a tube stabilizer plate having a plurality of tube through-holes. A plurality of flow-restricting devices is disposed on the tube restrictor plate adjacent to the plurality of tube through-holes. The tube management device further includes a multi-position switch. A plurality of tubes pass through the tube through-holes. Moreover, setting the multi-position switch to a first position causes the plurality of flow-restricting devices to restrict the flow in a first subset of the plurality of tubes to transfer tissue from a patient to the interior volume, setting the multi-position switch to a second position causes the plurality of flow-restricting devices to restrict the flow in a second subset of the plurality of tubes to allow processing of the tissue in the interior volume, and setting the multi-position switch to a third position causes the plurality of flow-restricting devices to restrict the flow in a third subset of the plurality of tubes to allow transfer of the tissue out of the interior volume.

In an embodiment of the present invention, a method of managing surgical conduits is described. The method provides a plurality of tubes and a plurality of flow-restricting devices within a body, each of the flow-restricting devices proximal to at least one of the plurality of tubes. The method also provides a multi-position switch wherein flow in a first subset of the plurality of tubes is restricted by the plurality of flow-restricting devices when the multi-position switch is in a first position and flow in a second subset of the plurality of tubes different than the first subset is restricted by the plurality of flow-restricting devices when the multi-position switch is in a second position. The method also switches from the first position of the multi-position switch to the second position of the multi-position switch.

In an embodiment of the present invention, a tube management device includes a tube restrictor plate having a plurality of tube through-holes and a tube stabilizer plate having a plurality of tube through-holes. A plurality of flow-restricting devices is disposed on the tube restrictor plate adjacent to the plurality of tube through-holes. The tube management device also includes a multi-position switch and a plurality of tubes that pass through the pluralities of tube through-holes. Setting the multi-position switch of the tube management device to a first position causes the plurality of flow-restricting devices to restrict the flow in a first subset of the plurality of tubes, setting the multi-position switch to a second position causes the plurality of flow-restricting devices to restrict the flow in a second subset of the plurality of tubes, and setting the multi-position switch to a third position causes the plurality of flow-restrictring devices to restrict the flow in a third subset of the plurality of tubes.

BRIEF DESCRIPTION OF THE DRAWINGS

FIG. 4 illustrates a decision matrix for determining the status of assorted system inputs in an exemplary tissue transfer system as described in various embodiments;

DESCRIPTION OF EXEMPLARY EMBODIMENTS

Figure 1:
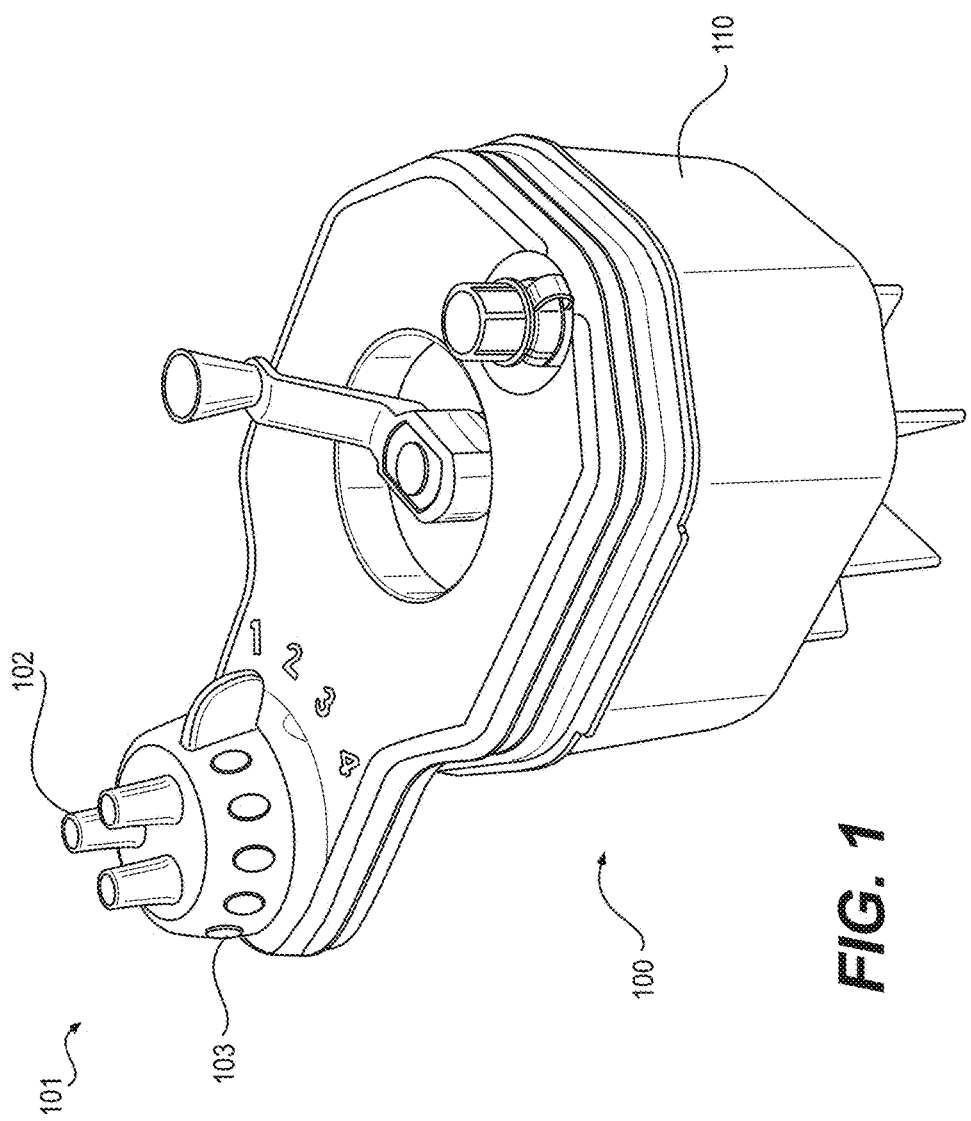
FIG. 1 illustrates a tissue treatment system according to various embodiments.

Reference will now be made in detail to certain exemplary embodiments according to the present disclosure, certain examples of which are illustrated in the accompanying drawings. Wherever possible, the same reference numbers will be used throughout the drawings to refer to the same or like parts.

In this application, the use of the singular includes the plural unless specifically stated otherwise. In this application, the use of "or" means "and/or" unless stated otherwise. Furthermore, the use of the term "including", as well as other forms such as "included" and "includes", is not limiting. The section headings used herein are for organizational purposes only and are not to be construed as limiting the subject matter described. All documents, or portions of documents, cited in this application including but not limited to patents, patent applications, articles, books, and treatises are hereby expressly incorporated by reference in their entirety for any purpose.

As used herein, "adipose tissue" refers to adipose tissue obtained by any means including, for example, liposuction and/or tumescent liposuction. In addition, the adipose tissue may be substantially intact or may be altered by, for example, washing with saline, antimicrobials, detergents, or other agents; the addition of therapeutic agents such an analgesics, antimicrobials, and anti-inflammatories; the removal of some cells or acellular components; or disruption or alteration by the collection process itself including, for example, during liposuction or tumescent liposuction. The adipose tissue can be autologous tissue, allogeneic tissue, or xenogenic tissue (e.g., porcine tissue).

As described above, some surgical procedures require use of tubes, hoses, or other conduits to transfer fluids, gases, and/or tissue products between a patient and a treatment system or device; or among systems and devices. Multi-step procedures are not uncommon and may require connection and disconnection of hoses from input and output ports. For example, a system for adipose tissue transfer and processing (e.g., adipose washing) can require over one hundred combined user actions and decisions, including enabling and disabling vacuum sources or adding or removing tissue or washing solutions to a tissue storage and treatment container. The maintenance and verification of tube connections during a medical procedure can be non- trivial, especially when the procedure has a time-sensitive component.

Various human and animal tissues can be used to produce products for treating patients. For example, various tissue products have been produced for regeneration, repair, augmentation, reinforcement, and/or treatment of human tissues that have been damaged or lost due to various diseases and/or structural damage (e.g., from trauma, surgery, atrophy, and/or long-term wear and degeneration). Fat grafting, including autologous fat grafting, can be useful for a variety of clinical applications including facial fillers, breast augmentation, buttock augmentation/sculpting, augmentation of other tissue sites, correction of lumpectomy defects, cranialfacial defect correction, and correction of lipoplasty defects (divots).

To prepare tissue for autologous fat grafting, tissue cleaning and processing must be performed. The process of grafting typically involves steps such as removal of tissue from a patient with a syringe or cannula. This tissue is pulled into a tissue processing container where unwanted components of the tissue can be separated and/or the tissue can be cleaned using various solutions. A typical system might include meshes for filtration and separation, cranks connected to mixing blades, and several input and output ports. Once the tissue is sufficiently prepared, it must be removed from the container and be injected or grafted back into the patient. During transfer steps, vacuum devices help move the tissue from location to location. However, it is desirable to disconnect the vacuum pressure during processing steps. In addition, the tissue-carrying tubes that are not in use during any given step should be blocked to maintain the sterility of the system.

Turning to FIG. 1, an illustrative embodiment of a tissue treatment system 100 is shown. As shown, the tissue treatment system 100 can include a container having an exterior wall 110 surrounding an interior volume. The interior of the container can also contain filters, mixing blades, hoses, and other components to enable washing and conditioning of tissue. The system 100 can include a tube management device 101 to facilitate operation of the system 100. Tubes can pass from the exterior of the system 100 to the interior through ports 102 of the tube management device 101, and tube restrictor devices (discussed below) within the tube management device 101 can control which tubes are open and which are blocked for a given system configuration. The system configuration is determined by the setting of a multi-position switch 103. In some embodiments, the system 100 can be provided with a carry handle for convenient handling by a user.

As used herein, the terms "tube," "hose," "conduit," or similar language will be used interchangeably and will be understood to refer to any passageway having a lumen configured to allow passage or fluids, gases, and/or tissue products therethrough.

Figure 2:
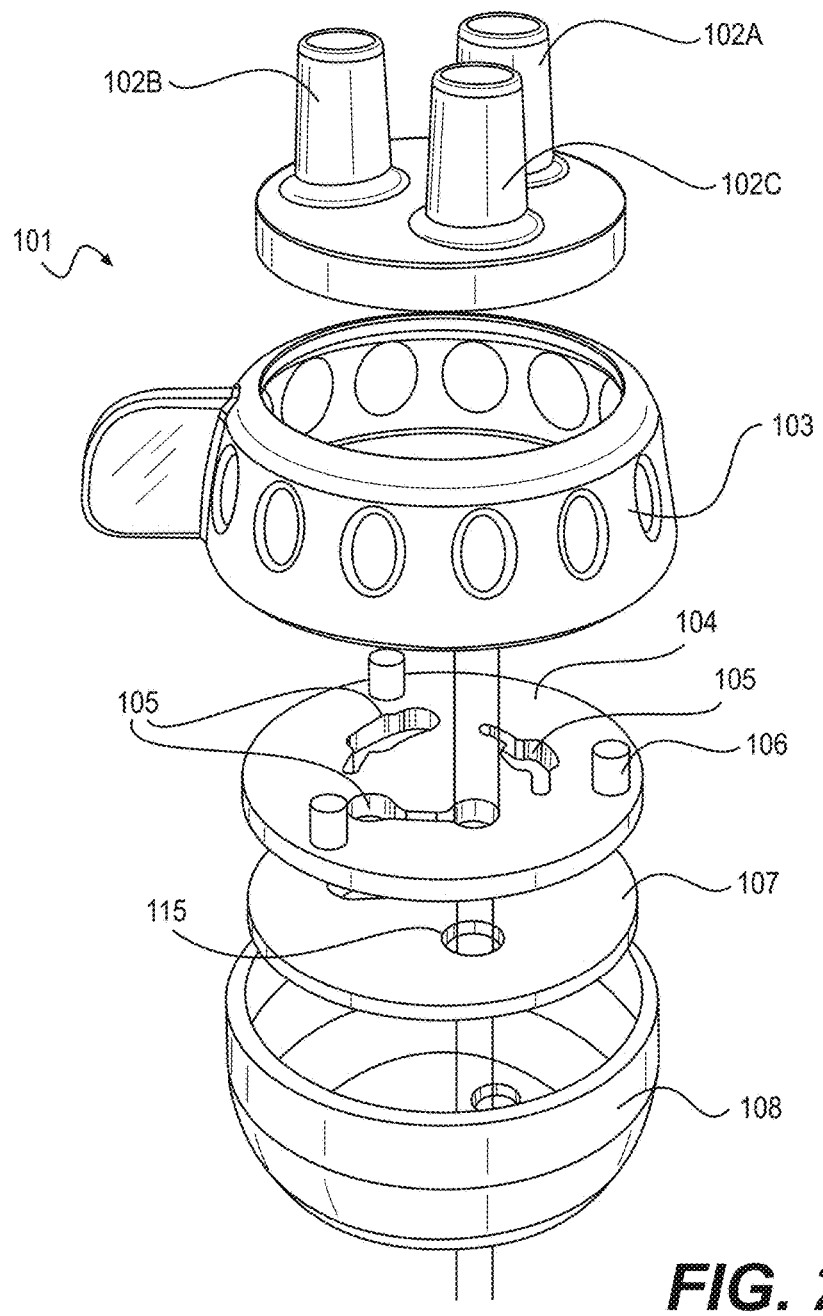
FIG. 2 is an exploded view of a tube management device according to various embodiments.

An exploded view of one embodiment of a tube management device 101 is shown in FIG. 2. The tube management device 101 may include ports 102a, 102b, 102c and a multi-position switch 103. Tubes can pass through the ports 102a, 102b, 102c and then through a tube restrictor plate 104 and a tube stabilizer plate 107 before passing out of the device 101. Based on the position of the multi-position switch 103, restrictor elements 105 on the tube restrictor plate 104 can allow or obstruct flow through each of the tubes. In some embodiments, the contents of the tube management device 101 can be contained within an exterior wall 108 that forms a body. In alternate embodiments, the components of the tube management device 101 can be attached directly to the structure of the container 110.

The ports 102a, 102b, 102c can have a variety of configurations. In accordance with various embodiments, the ports 102a, 102b, 102c may be straight-walled or barbed; threaded or unthreaded; and have no fittings, luer fittings, swaged fittings, or any other type of connector suitable for a specific application. Although the ports 102a, 102b, 102c are depicted as extending out from the body of the tube management device 101, the ports may also be threaded or unthreaded holes or recesses or may extend inward from the surface into the body of the device 101. Although only three ports are depicted in FIG. 2, any number of ports can be chosen to match the number of tubes needed in a particular application. Substances including, but not limited to, gases, liquids, chemical solutions, and biological tissues can flow into or out from the ports 102a, 102b, 102c depending upon the position of the multi-position switch and the requirements of any particular step of the medical procedure.

The position of the multi-position switch 103 can be used to switch among different device configurations. In some embodiments, the multi-position switch 103 is a rotating body or knob and the rotational angle of the body determines the switch state. In accordance with various embodiments, the multi-position switch 103 may be any mechanical or electronic switch (including rotational or linear throw switches) that, through appropriate linkages, can alter the state of openness of tubes passing through the device. In some embodiments, the multi-position switch 103 can include non-slip grips or similar features to facilitate easier operation by a user, in particular by a user wearing surgical gloves. The positions of the multi-position switch 103 may correspond to steps in a procedure. For example, the steps in a procedure might include liposuction/tissue extraction, hold and mix, irrigation, and vacuum/clear steps.

Figure 3:
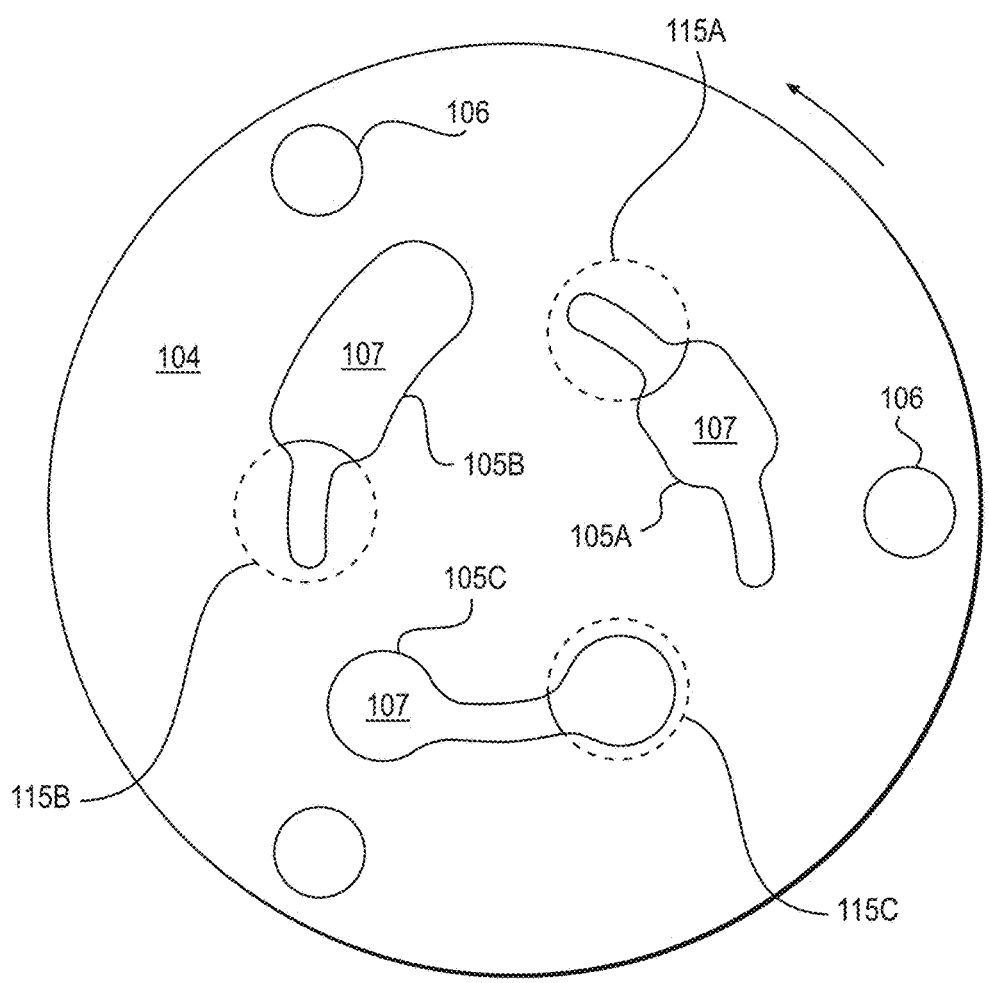
FIG. 3 is a top view of one embodiment of a tube restrictor plate and a tube stabilizer plate, which are components of a tube management system according to the present invention.

The tube restrictor plate 104 can block or allow flow through tubes that pass through the tube through-holes of the plate through the use of flow-restricting devices. In accordance with various embodiments, and as depicted in FIGS. 2 and 3, the tube restrictor plate 104 may be provided with flow-restricting devices 105 in the form of contoured radial slots. The slots 105 can have a slot width that varies according to the desired action of the slot upon a tube for each angular position of the tube restrictor plate 104. For example, each slot 105 may include two slot widths that correspond to unrestricted flow in a tube and complete blockage of flow in a tube. Alternatively, each slot may have a range of widths corresponding to different levels of flow restriction.

In FIG. 3, a tube restrictor plate 104 is shown overlaid upon a tube stabilizer plate 107 with slots 105a, 105b, 105c indicated. The example embodiment of a tube restrictor plate 104 shown in FIG. 3 illustrates tube through-holes in the form of contoured radial slots 105a, 105b, 105c suitable for a tube management device 101 having a multi-position switch 103 with three positions. The contoured radial slots 105a, 105b, 105c of the tube restrictor plate 104 are overlaid in this top view on the tube through-holes 115a, 115b, 115c of the tube stabilizer plate 107. In this figure, the position of tube restrictor plate 104 with respect to tube stabilizer plate 107 places slots 105a, 105b, 105c in the first position over tube through-holes 115a, 115b, 115c. Activation of the multi-position switch can cause the tube restrictor plate 104 to rotate in the direction shown by the arrow while the tube stabilizer plate 107 stays in place. As a result, the radial slots can advance to the second or third position as needed. In accordance with various embodiments, the system 100 can be provided with a plurality of tube restrictor plates 104 having different arrangements of slots 105a, 105b, 105c intended for different procedures having different steps. In these embodiments, the user may choose one of the plurality of tube restrictor plates 104 to place within the body 108 of the device 101 depending upon the application.

The tube restrictor plate 104 may have locating features 106 that can interlock with the multi-position switch 103. The locating features 106 can help the user align the tube restrictor plate with the multi-position switch 103 and within the tube management device 101 so that the contoured radial slots 105a, 105b, 105c are properly in-line with their respective ports 102a, 102b, 102c. In addition, the locating features 106 can match with complementary features on the multi-position switch so that the switch's position reflects the proper tubing state within the tube management device 101. In some embodiments, the locating features 106 can fix the multi-position switch 103 to the tube restrictor plate 104 such that they move in concert when the switch is rotated.

The tube management device 101 can have a tube stabilizer plate 107. The tube stabilizer plate 107 may have tube through-holes 115 to allow tubes to pass therethrough. In some embodiments, the diameter of each of the tube through-holes 115 in the tube stabilizer plate 107 may be equal or approximately equal to the outer diameter of the corresponding tube that passes through the hole 115 to provide a secure fit around the outside of each tube without compression. The tube stabilizer plate 107 can hold the tube in position so that activation or movement of the tube restrictor plate 104 cannot twist, reorient, or move the tubes.

As discussed above, the system 100 can be used to operate surgical systems, such as adipose tissue transfer systems. Accordingly, an exemplary decision matrix 400 for an adipose tissue transfer process is shown in FIG. 4. The decision matrix may be used to determine the open/closed status of any tubes in the system during any steps of an adipose transfer procedure. In some embodiments, a tissue treatment system 100 similar to that shown in FIG. 1 can have 4 tube inputs that are either open or blocked during a given step of a medical procedure. In a liposuction or aspiration 402 step, the tube to the liposuction cannula and the vacuum tube may be open while the irrigation tube and vent tube are closed. In a hold and mix or washing 404 step, all 4 inputs can be blocked. In an irrigation or transfer 406 step, the tube to the liposuction cannula and the vacuum tube may be closed while the irrigation tube and the vent tube can be open. In a vacuum/clear 408 step, the tube to the liposuction cannula and the irrigation tube may be closed while the vacuum tube and the vent tube can be open.

Figure 5:
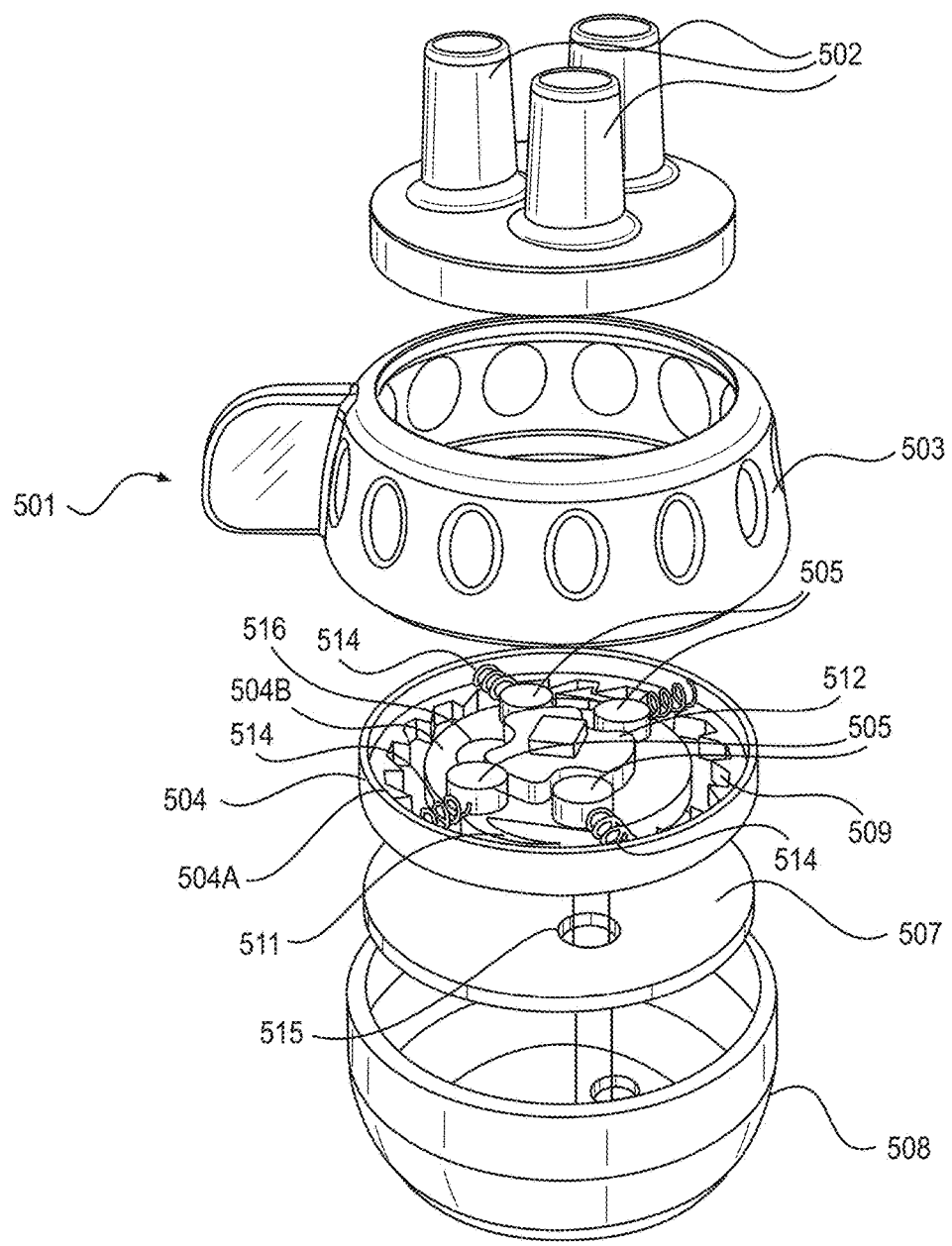
FIG. 5 is an exploded view of an alternative tube management device according to the present invention.

An alternate embodiment of a tube management device 501 is shown in FIG. 5. The tube management device 501 can include ports 502 and a multi-position switch 503. Tubes can pass from the ports 502 through a tube restrictor plate 504 and a tube stabilizer plate 507 before passing out of the device 501. Based on the position of the multi-position switch, restrictor elements 505 on the tube restrictor plate 504 can allow or obstruct flow through each of the tubes. The contents of the tube management device 501 can be contained within an exterior wall 508 that forms a body.

As with the previously discussed embodiments, the ports can have a variety of configurations. For example, the ports 502 may be straight-walled or barbed; threaded or unthreaded; and have no fittings, luer fittings, swaged fittings, or any other type of connector demanded by application-specific requirements. Although ports 502 are depicted in this embodiment as extending out from the body of the tube management device 501, the ports may also be threaded or unthreaded recesses or holes or may extend inward from the device surface into the body of the device 501. Although only three ports are depicted in FIG. 5, any number of ports can be chosen to match the number of tubes needed in a particular application. Substances including, but not limited to, gases, liquids, chemical solutions, and biological tissues can flow into or out from the ports 502 depending upon the position of the multi-position switch and the requirements of any particular step of the surgical procedure.

The positions of the multi-position switch 503 can be used to switch among different device configurations. In some embodiments, the multi-position switch 503 is a rotating body or knob and the rotational angle of the body determines the switch state. In accordance with various embodiments, the multi-position switch 503 may be any mechanical or electronic switch (including rotational or linear throw switches) that, through appropriate linkages, can alter the state of openness of tubes passing through the device. In some embodiments, the multi-position switch 503 can include non-slip grips or similar features to facilitate easier operation by a user, in particular by a user wearing surgical gloves. The positions of the multi-position switch 503 may correspond to steps in a procedure. For example, the steps in a procedure might include liposuction/tissue extraction, hold and mix, irrigation, and vacuum/clear steps.

The tube restrictor plate 504 can block or allow flow through the tubes that pass through the tube through-holes 516 of the plate through the use of flow-restricting devices. The tube restrictor plate 504 may include an external ring 504a that is rotatably engaged with a central portion 504b. Tubes can pass through the tube restrictor plate 504 through tube through-holes 516 adjacent to flow-restricting devices. In accordance with various embodiments and as depicted in FIG. 5, the tube restrictor plate 504 may be provided with flow-restricting devices in the form of a contoured central hub 512 on the central portion 504b and sliding blocks 505 that force the tubes against the hub 512 via the integrated springs 514 attached to the external ring 504a. The sliding blocks 505 may be shaped as flat plates, cylinders, ovals, spheres, ovoid configuration, or any other shape that meets application-specific requirements. In some embodiments, the contoured central hub 512 may have an equal number of recesses to the number of ports 502, and each tube may pass through a tube through-hole 516 adjacent to a recess of the contoured central hub. When a sliding block 505 attached to an integrated spring 512 is in line with a recess of the contoured central hub 512, the force of the spring may extend the sliding block and force it against a tube. In some embodiments, the central portion 504b of the tube restrictor plate 504 may be fixedly attached to the tube stabilizer plate 507. As the multi-position switch 503 changes from one position to another, the external ring 504a of the tube restriction plate 504 may rotate while the central portion 504b containing the contoured central hub 512 does not rotate relative to the tube stabilizer plate 507.

In accordance with various embodiments, the external ring 504a may be provided with a one-way ratcheting mechanism 509. The teeth of the ratcheting mechanism can engage with a pawl 511 positioned on the central portion 504b of the tube restriction plate 504 such that rotation of the external ring 504a is allowed in one direction but prevented in the opposite direction. Although the pawl 511 is depicted as being located on the central portion 504b in this embodiment, it will be apparent to those of ordinary skill in the art that the pawl could be attached at other points throughout the tube management device 501 such as the interior of the multi-position switch 503 or the tube stabilizer plate 507.

The tube management device 501 can also include a tube stabilizer plate 507. The tube stabilizer plate 507 may have tube through-holes 515 to allow tubes to pass through. In some embodiments, the diameter of each of the tube through-holes 515 in the tube stabilizer plate 507 may be equal to the outer diameter of the corresponding tube that passes through the hole to provide a secure fit around the outside of each tube without compression. The tube stabilizer plate 507 can hold the tube in position so that activation or movement of the tube restrictor plate 504 cannot twist, reorient, or move the tubes.

Figure 6:
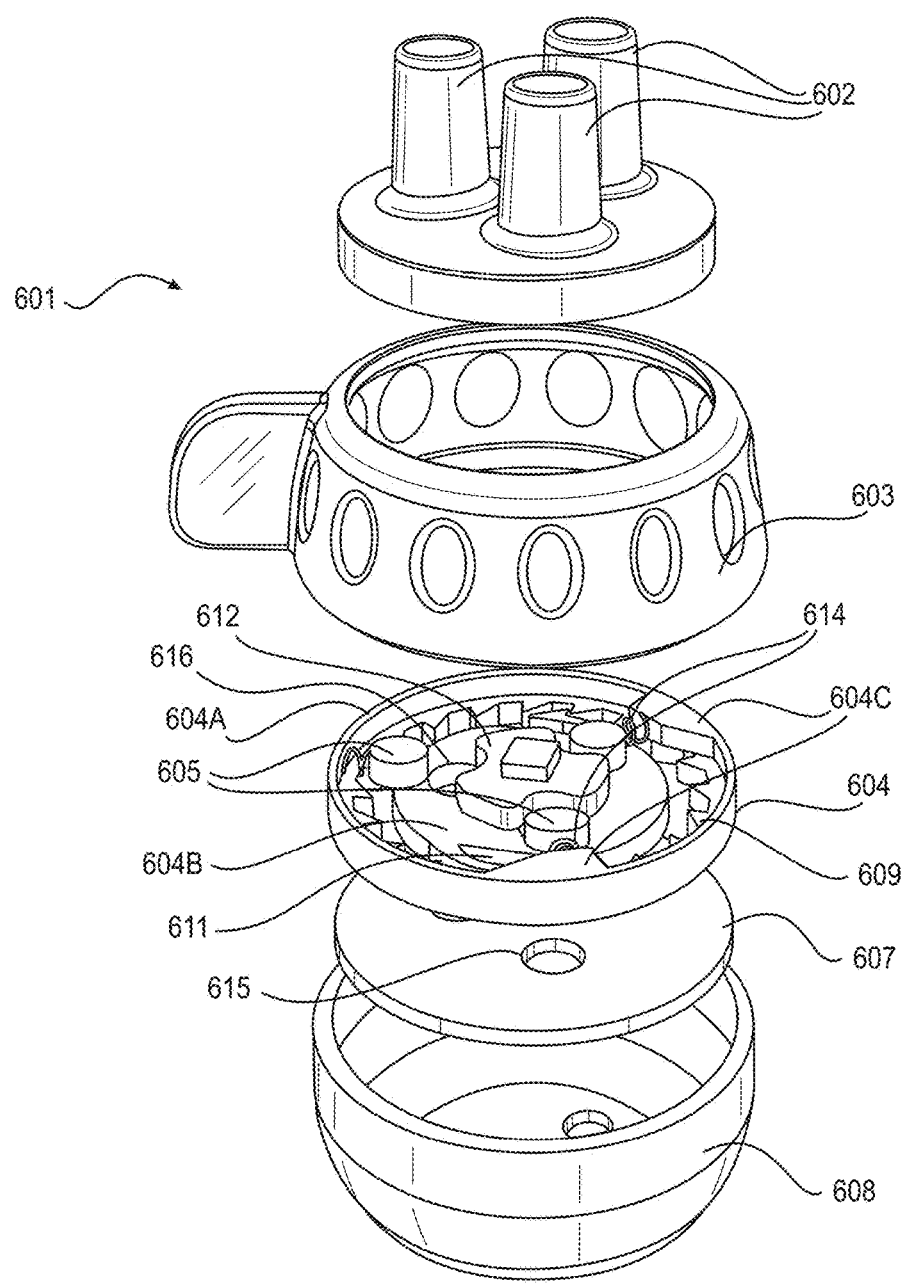
FIG. 6 illustrates a variant of the tube management device displayed in FIG. 5 according to various embodiments.

Another embodiment of a tube management device is shown in FIG. 6. The tube management device 601 can include ports 602 and a multi-position switch 603. The device 601 can include a tube stabilizer plate 607 and a tube restrictor plate 604 containing flow restriction devices. The components of the device 601 can be enclosed within a body 608.

The ports 602 are the connection between the tube management device 601 and the exterior world. In accordance with various embodiments, the ports 602 may be straight-walled or barbed; threaded or unthreaded; and have no fittings, luer fittings, swaged fittings, or any other type of connector demanded by application-specific requirements. Although the ports 602 are depicted in this embodiment as extending out from the body of the tube management device 601, the ports may also be threaded or unthreaded holes or may extend inward from the device surface into the body of the device 601. Although only three ports are depicted in FIG. 6, it will be evident to one of ordinary skill in the art that any number of ports 602 can be chosen to match the number of tubes needed in a particular application. Fluids including, but not limited to, gases, liquids, chemical solutions, and biological tissues can flow into or out from the ports 602 depending upon the position of the multi-position switch and the requirements of any particular step of the medical procedure.

The positions of the multi-position switch 603 can be used to switch among different device configurations. In some embodiments, the multi-position switch 603 is a rotating body or knob and the rotational angle of the body determines the switch state. In accordance with various embodiments, the multi-position switch 603 may be any mechanical or electronic switch (including rotational or linear throw switches) that, through appropriate linkages, can alter the state of openness of tubes passing through the device. In some embodiments, the multi-position switch 603 can include non-slip grips or similar features to facilitate easier operation by a user, in particular by a user wearing surgical gloves. The positions of the multi-position switch 603 may correspond to steps in a procedure. For example, the steps in a procedure might include liposuction/tissue extraction, hold and mix, irrigation, and vacuum/clear steps.

The tube restrictor plate 604 may include an external ring 604a that is rotatably engaged with a central portion 604b. Tubes may pass through tube through-holes 616 adjacent to flow-restricting devices. In accordance with various embodiments and as depicted in FIG. 6, the tube restrictor plate 604 may be provided with flow-restricting devices in the form of a contoured central hub 612 on the central portion 604b and sliding blocks 605 that force the tubes against the hub 612 via the integrated springs 614 attached to the external ring 604a. The sliding blocks 605 may be shaped as flat plates, cylinders, ovals, spheres, eggs, or any other shape that meets application-specific requirements. In some embodiments, the contoured central hub 612 may have an equal number of recesses to the number of ports 602, and each tube may pass through a tube through-hole 616 adjacent to a recess of the contoured central hub. When a sliding block 605 attached to an integrated spring 612 is in line with a recess of the contoured central hub 612, the force of the spring may extend the sliding block and force it against a tube. As the multi-position switch 603 changes from one position to another, the external ring 604a of the tube restriction plate 604 may rotate while the central portion 604b containing the contoured central hub 612 does not rotate relative to the tube stabilizer plate 607. In accordance with various embodiments, the sliding blocks 605 and integrated springs 614 can be placed at different radial depths using spacers 604c.

The tube management device 601 can have a tube stabilizer plate 607 in some embodiments. The tube stabilizer plate 607 may have tube through-holes 615 to allow tubes to pass through. In preferred embodiments, the diameter of each of the tube through-holes 615 in the tube stabilizer plate 607 may be equal to the outer diameter of the corresponding tube that passes through the hole to provide a secure fit around the outside of each tube without compression. The tube stabilizer plate 607 can hold the tube in position so that activation or movement of the tube restrictor plate 604 cannot twist, reorient, or move the tubes.

Figure 7:
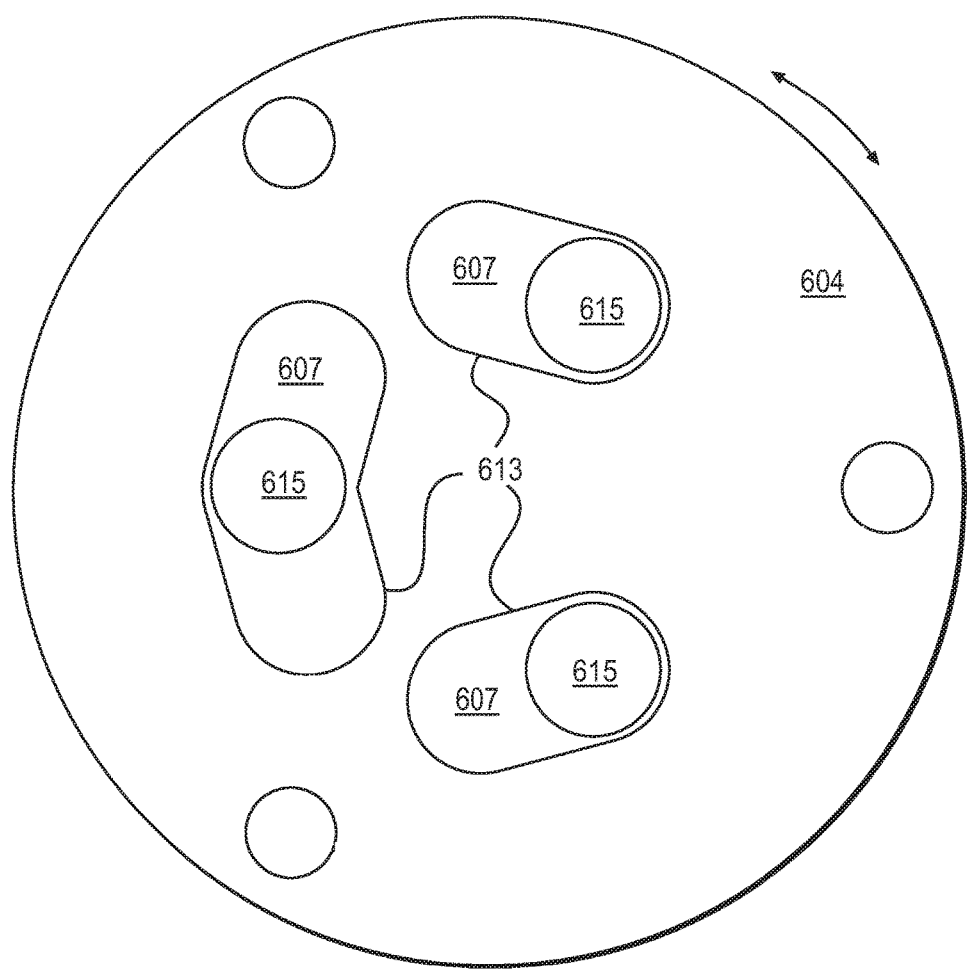
FIG. 7 is a top view of a tube restrictor plate and a tube stabilizer plate of the tube management device of the embodiment shown in FIG. 6.

A top view of the tube restrictor plate 604 overlaid on tube stabilizer plate 607 of the embodiment of FIG. 6 is shown in FIG. 7. In accordance with various embodiments, the tube restrictor plate 604 can have slots 613 to allow the tubes to change position with respect to the contoured central hub 612 of the central portion 604b and the associated flow-restricting devices. In this way, a single embodiment of the tube restrictor plate 604 can be used in more than one configuration. When a tube is in an "in" position, the tube passes near a recess of the contoured central hub 612 and can be closed by sliding blocks 605 attached to spacers 604c extending from the external ring 604a. When a tube is in an "out" position, the tube passes near an extended portion of the contoured central hub 612. In this position, the tube can be closed by sliding blocks 505 that are attached by integrated springs 614 directly to the external ring 604a. In a preferred embodiment, sliding blocks 605 attached directly to the external ring 604a without spacers 604c cannot reach tubes adjacent to recesses of the contoured central hub 612.

In accordance with various embodiments, the external ring 604a may be provided with a one-way ratcheting mechanism 609. The teeth of the ratcheting mechanism can engage with a pawl 611 positioned on the central portion 604b of the tube restriction plate 604 such that rotation of the external ring 604a is allowed in one direction but prevented in the opposite direction. Although the pawl 611 is depicted as being located on the central portion 604b in this embodiment, it will be apparent to those of ordinary skill in the art that the pawl could be attached at other points throughout the tube management device 601 such as the interior of the multi-position switch 603 or the tube stabilizer plate 607.

A method of managing surgical conduits is also envisioned by the inventors. The method includes providing several tubes and several flow-restricting devices within a body where each of the flow-restricting devices is proximal to at least one of the tubes and providing a multi-position switch wherein the flow in a first subset of the tubes is restricted by the flow-restricting devices when the switch is in a first position and flow in a second subset of tubes different than the first subset is restricted by the flow-restricting devices when the switch is in a second position. The method concludes by switching from the first position of the multi-position switch to the second position.

The step of providing several tubes and several flow-restricting devices within a body where each of the flow-restricting devices is proximal to at least one of the tubes may include, but is not limited to, passing tubes through ports 102 and past flow-restricting devices 105 in a tube management device 101 as described above in connection with FIGS. 1-3.

The step of providing a multi-position switch wherein the flow in a first subset of the tubes is restricted by the flow-restricting devices when the switch is in a first position and flow in a second subset of tubes different than the first subset is restricted by the flow-restricting devices when the switch is in a second position may include, but is not limited to, providing a multi-position switch 103 in a tube management device 101 as described above in connection with FIGS. 1-3.

The step of switching from the first position of the multi-position switch to the second position may include, but is not limited to, switching a multi-position switch 103 from a first position to a second position as described above in connection with FIGS. 1 and 2.

Figure 8:
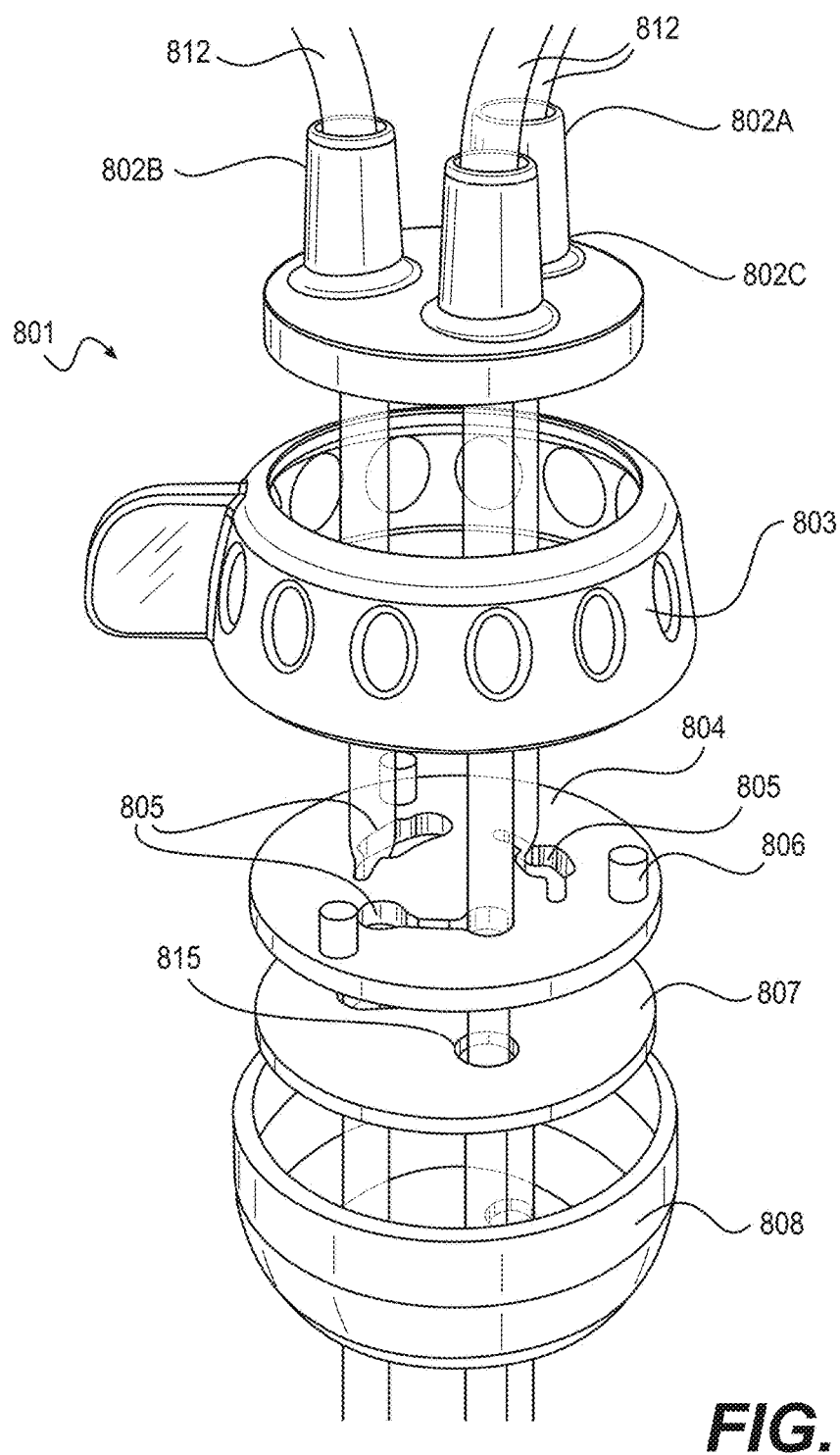
FIG. 8 illustrates a tube management device according to various embodiments.

An exploded view of an alternative embodiment of a tube management device 801 is shown in FIG. 8. The tube management device 801 may include ports 802a, 802b, 802c and a multi-position switch 803. Tubes 812 pass through the ports 802a, 802b, 802c and then through a tube restrictor plate 804 and a tube stabilizer plate 807 before passing out of the device 801. Based on the position of the multi-position switch 803, restrictor elements 805 on the tube restrictor plate 804 can allow or obstruct flow through each of the tubes 812. In some embodiments, the contents of the tube management device 801 can be contained within an exterior wall 808 that forms a body.

The ports 802a, 802b, 802c can have a variety of configurations as described previously with respect to FIG. 2. In accordance with various embodiments, the ports 802a, 802b, 802c may be straight-walled or barbed; threaded or unthreaded; and have no fittings, luer fittings, swaged fittings, or any other type of connector suitable for a specific application. Although the ports 802a, 802b, 802c are depicted as extending out from the body of the tube management device 801, the ports may also be threaded or unthreaded holes or recesses or may extend inward from the surface into the body of the device 801. Although only three ports are depicted in FIG. 8, any number of ports can be chosen to match the number of tubes 812 needed in a particular application. Substances including, but not limited to, gases, liquids, chemical solutions, and biological tissues can flow into or out of tubes 812 passing through the ports 802a, 802b, 802c depending upon the position of the multi-position switch and the requirements of any particular step of a medical procedure.

As described above with reference to FIG. 2, the position of the multi-position switch 803 can be used to switch among different device configurations. In some embodiments, the multi-position switch 803 is a rotating body or knob, and the rotational angle of the body determines the switch state. In accordance with various embodiments, the multi-position switch 803 may be any mechanical or electronic switch (including rotational or linear throw switches) that, through appropriate linkages, can alter the state of openness of the tubes 812. In some embodiments, the multi-position switch 803 can include non-slip grips or similar features to facilitate easier operation by a user, in particular by a user wearing surgical gloves. The positions of the multi-position switch 803 may correspond to steps in a procedure. For example, the steps in a procedure might include liposuction/tissue extraction, hold and mix, irrigation, and vacuum/clear steps.

The tube restrictor plate 804 can block or allow flow through the tubes 812 as they pass through the plate through the use of flow-restricting devices. Similar to the embodiments depicted in FIGS. 2 and 3, the tube restrictor plate 804 may be provided with both flow-restricting devices and tube through-holes in the form of contoured radial slots 805. In alternative embodiments, the flow-restricting devices can be similar to those described above with reference to the embodiments of FIGS. 5 and 6. The slots 805 can have a slot width that varies according to the desired action of the slot upon a tube 812 for each angular position of the tube restrictor plate 804. For example, each slot 805 may include two slot widths that correspond to unrestricted flow in a tube 812 and complete blockage of flow in a tube 812. Alternatively, each slot may have a range of widths corresponding to different levels of flow restriction.

The tube restrictor plate 804 may have locating features 806 that can interlock with the multi-position switch 803. The locating features 806 can help the user align the tube restrictor plate 804 with the multi-position switch 803 and within the tube management device 801 so that the contoured radial slots 805 are properly in-line with their respective ports 802a, 802b, 802c. In addition, the locating features 806 can match with complementary features on the multi-position switch so that the switch's position reflects the proper tubing state within the tube management device 801. In some embodiments, the locating features 806 can fix the multi-position switch 803 to the tube restrictor plate 804 such that they move in concert when the switch is rotated.

The tube management device 801 can have a tube stabilizer plate 807. The tube stabilizer plate 807 may have tube through-holes 815 to allow tubes to pass therethrough. In some embodiments, the diameter of each of the tube through-holes 815 in the tube stabilizer plate 807 may be equal or approximately equal to the outer diameter of the corresponding tube that passes through the hole to provide a secure fit around the outside of each tube without compression. The tube stabilizer plate 807 can hold the tube in position so that activation or movement of the tube restrictor plate 804 cannot twist, reorient, or move the tubes.

The tubes 812 of tube management device 801 can be made of any material that meets application-specific requirements. The tubes 812 may be made of, for example but not limited to, PVC, high-density polyethylene, nylon, latex, silicone, polyurethane, TYGON®, or any non-reactive tubing or hose. As depicted in FIG. 8, the tubes 812 may extend out of the ports 802a, 802b, 802c or may terminate within or below the ports 802a, 802b, 802c. The tubes 812 may be permanently attached to the tube management device 801, for example, at the ports 802a, 802b, 802c or body 808, or the tubes 812 may be removable and/or replaceable. In accordance with various embodiments, the tubes 812 may be disposed of after each procedure and replaced with new tubes 812 to allow for reuse of tube management device 801 for multiple procedures.

While the present invention has been described herein in conjunction with preferred embodiments, a person of ordinary skill in the art can effect changes, substitutions or equivalents to the systems and methods described herein, which are intended to fall within the appended claims and any equivalents thereof.

The invention claimed is:

1. A tissue treatment system, comprising:
a container, including:
an exterior wall surrounding an interior volume for holding tissue; and
a filter for processing tissue;
a tube management device, including:
a tube restrictor plate having a plurality of tube through-holes;
a tube stabilizer plate having a plurality of tube through-holes;
a plurality of flow-restricting devices disposed on the tube restrictor plate adjacent to the plurality of tube through-holes; and
a multi-position switch;
wherein a plurality of tubes passes through the pluralities of tube through-holes, and
wherein setting the multi-position switch to a first position causes the plurality of flow-restricting devices to restrict the flow in a first subset of the plurality of tubes to transfer tissue from a patient to the interior volume, setting the multi-position switch to a second position causes the plurality of flow-restricting devices to restrict the flow in a second subset of the plurality of tubes to allow processing of the tissue in the interior volume, and setting the multi-position switch to a third position causes the plurality of flow-restricting devices to restrict the flow in a third subset of the plurality of tubes to allow transfer of the tissue out of the interior volume.

2. The system of claim 1, wherein the plurality of flow-restricting devices includes contoured radial slots located on the tube restrictor plate.

3. The system of claim 2, wherein the tube restrictor plate is chosen from a set of tube restrictor plates having at least two plates with differently contoured radial slots.

4. The system of claim 1, wherein the one or more flow-restricting devices include a plurality of sliding blocks, a subset of the plurality of sliding blocks being engaged to restrict flow within a first subset of the plurality of tubes.

5. The system of claim 1, further comprising a carry handle.

6. The system of claim 1, wherein the multi-position switch is configured to allow switching in only one direction.

7. The system of claim 6, further comprising a ratchet mechanism to allow the multi- position switch to move in only one direction.

8. The system of claim 1, further comprising at least one of a mixing blade or filter to facilitate tissue washing or treatment.

9. The system of claim 1, wherein the positions of the multi-position switch correspond to process steps in a tissue washing or processing procedure.

10. The system of claim 9, wherein at least one position of the multi-position switch corresponds to a tissue aspiration step of the tissue washing or processing procedure.

11. The system of claim 9, wherein at least one position of the multi-position switch corresponds to a tissue washing step of the tissue washing or processing procedure.

12. The system of claim 9, wherein at least one position of the multi-position switch corresponds to a step of the tissue washing or processing procedure wherein tissue is transferred out of the container.

13. The system of claim 1, further comprising the plurality of tubes that pass through the plurality of tube through-holes.

14. A tube management device, comprising:
a tube restrictor plate having a plurality of tube through-holes;
a tube stabilizer plate having a plurality of tube through-holes;
a plurality of flow-restricting devices disposed on the tube restrictor plate adjacent to the plurality of tube through-holes;
a multi-position switch; and
a plurality of tubes that pass through the pluralities of tube through-holes, and
wherein setting the multi-position switch to a first position causes the plurality of flow-restricting devices to restrict the flow in a first subset of the plurality of tubes, setting the multi-position switch to a second position causes the plurality of flow-restricting devices to restrict the flow in a second subset of the plurality of tubes, and setting the multi-position switch to a third position causes the plurality of flow-restricting devices to restrict the flow in a third subset of the plurality of tubes.

15. The device of claim 14, wherein the plurality of flow-restricting devices includes contoured radial slots located on the tube restrictor plate.

16. The device of claim 15, wherein the tube restrictor plate is chosen from a set of tube restrictor plates having at least two plates with differently contoured radial slots.

17. The device of claim 14, wherein the one or more flow-restricting devices include a plurality of sliding blocks, a subset of the plurality of sliding blocks being engaged to restrict flow within a first subset of the plurality of tubes.

18. The device of claim 14, wherein the multi-position switch is configured to allow switching in only one direction.

19. The device of claim 18, further comprising a ratchet mechanism to allow the multi- position switch to move in only one direction.

20. The device of claim 14, wherein the positions of the multi-position switch correspond to process steps in a tissue washing or processing procedure.

21. The device of claim 20, wherein at least one position of the multi-position switch corresponds to a tissue aspiration step of the tissue washing or processing procedure.

22. The device of claim 20, wherein at least one position of the multi-position switch corresponds to a tissue washing step of the tissue washing or processing procedure.

23. The device of claim 20, wherein at least one position of the multi-position switch corresponds to a step of the tissue washing or processing procedure wherein tissue is transferred out of the container.

* * * * *